United States Patent
Batdorf, Sr.

[11] Patent Number: 6,117,170
[45] Date of Patent: Sep. 12, 2000

[54] SCLERAL BAND AND METHOD FOR MAKING

[75] Inventor: David B. Batdorf, Sr., Templeton, Calif.

[73] Assignee: Specialty Silicone Fabricators, Inc., Paso Robles, Calif.

[21] Appl. No.: 09/099,637

[22] Filed: Jun. 18, 1998

[51] Int. Cl.[7] .......................................................... A61F 2/14
[52] U.S. Cl. ................................... 623/4; 623/66; 602/41
[58] Field of Search ........................... 623/4, 66; 602/41, 602/42, 45, 46

[56] References Cited

U.S. PATENT DOCUMENTS

| | | | |
|---|---|---|---|
| 5,196,005 | 3/1993 | Doiron et al. | 606/7 |
| 5,511,965 | 4/1996 | Batdorf et al. | 425/381 |

*Primary Examiner*—Mickey Yu
*Assistant Examiner*—Dinh X. Nguyen
*Attorney, Agent, or Firm*—Michael G. Petit

[57] ABSTRACT

An elongate elastomeric band having unitary construction which construction includes a silicone sponge differentially compressive portion disposed along the length thereof. The band is dimensioned to encircle the eye of a patient having a detached retina. In use, the band is placed around the eye and surgically attached thereto in an encircling position. The band circumferentially deforms the sclera, particularly the portion of the sclera overlying the area of retinal detachment, the differentially compressive portion forcing the choroid and detached portion of the retina into juxtaposition for reattachment. The band, which includes a closed-cell silicone foam differentially compressive portion along a section of its length, is manufactured by means of extrusion providing an elastomeric, preferably silicone, band having unitary construction and varying in both its outer dimension and its compressibility along the length thereof. The transition in the outer dimension of the surface of the band along the band's length is gradual; tapering smoothly from the bulbous differentially compressive portion which has the greatest outer circumference to the relatively slender elastic band portion overlying and projecting outwardly from both ends of the differentially compressive portion. The band is made by simultaneously co-extruding a relatively non-compressible silicone elastomer and a silicone foam elastomer through a single die orifice having a controllable and variable shape and size followed by vulcanization of the extruded article.

5 Claims, 2 Drawing Sheets

SCLERAL BAND AND METHOD FOR MAKING

BACKGROUND OF THE INVENTION

1. Field of the Invention

A band for reattachment of the retina of an eye by means of scleral buckling.

2. Prior Art

Retinal detachment is a pathological disorder which occurs when there is a separation of two adjacent layers (the neurosensory retina and the retinal pigment epithileum) within the eye which normally remain in apposition. This disorder, if not detected early and treated, results in partial or total blindness. Retinal detachment may be preceded by a visual perception of a shower of "sparks" or "lightening flashes" and may be accompanied by a shower of "floaters". Floaters are perceived as spots before one or both eyes.

In a healthy individual, the vitreous choroid functions to give shape to the eye, aids in the transmission of light from the lens to the retina and may provide support to maintain the retina against the underlying retinal pigment epithelial layer. When an individual ages, the vitreous choroid may become liquefied at the retina-vitreal interface with consequent pulling away from the retina. This can result in a tear or retinal break. Continued traction upon the retinal break can result in the passage of vitreous fluid through the retinal break and under the retina resulting in retinal detachment.

Methods for treating retinal detachment are known in the prior art. Such methods include the removal of the vitreous gel from the eye and/or the injection of a gas into the vitreal chamber (pneumatic retinopexy) to seal a retinal detachment or tear in the upper region of the eye where the gas is used to apply pressure against the retina. If detachment has occurred, the pressure of the gas can hold the retina against the subjacent or underlying tissue and facilitate a reattachment of the retina to the subjacent tissue. Once the adjacent tissue layers are brought into juxtaposition, various treatment modalities may be used to create an adhesion between the retinal tear and the underlying tissue to assist in a more permanent attachment process which progresses with time. Such modalities include laser photocoagulation and or cryotherapy.

A procedure known as scleral bucking is also used to repair a detached retina. In this procedure, an elastic, compressive band is placed around the eye. A sponge or wedge is placed between the band and the portion of the sclera overlying the region of detachment. Tension on the band circumferentially compresses the sclera and deforms the eye, increasing the pressure of the vitreous humor and bringing the choroidal retinal pigment epithelial layer underlying the retina into juxtaposition. The band is held in an encircling position around the eye by means of a clasp affixed to the band to join opposing ends. In addition, a scleral buckling band may further include an inflatable balloon which may be positioned to overlie the area of detachment. Components of a scleral banding device minimally include a solid silicone band, a silicone member, preferably a sponge, and a clip for attaching the ends of band around the eye. Such scleral buckling band components are commercially available from: Mira, Inc., 87 Rumford Avenue, Waltham, Mass. 02154 and Stortz Instruments, St. Louis, Mo.

A problem associated with such prior art scleral buckling devices is that the (differentially compressive) silicone member may slip out from underneath the band during use. Thus, the silicone band and silicone differentially compressive member must both be sutured to the sclera of the eye to prevent the post-operative displacement of the compressive member overlying the retinal tear so that treatment is successful. In addition, the prior art scleral buckling devices present a more or less irregular, discontinuous surface to the sclera of the eye which, when the eye is compressed, may lead to undue and unwanted pressure applied to non-target areas of the sclera. It would, therefore, be desirable to provide a scleral buckling device wherein the differentially compressive portion and elastomeric band are unitary in construction. It would further be desirable to have the scleral-contacting surface of the band present minimum discontinuities or pressure points on non-target tissues of the eye.

SUMMARY OF THE INVENTION

It is an object of the invention to provide an elastomeric band for buckling the sclera of an eye thereby facilitating retinal reattachment.

It is a further object of the invention to provide a scleral buckling band having unitary construction and an elongate elastomeric encircling band portion and a differentially compressive portion disposed along a portion of the length of the encircling band portion.

It is yet another object of the invention to provide a unitary scleral buckling band wherein the change in outer dimension between the differentially compressive portion and the encircling band portion is smooth and continuously tapered.

The features of the invention believed to be novel are set forth with particularity in the appended claims. However the invention itself, both as to organization and method of operation, together with further objects and advantages thereof may be best be understood by reference to the following description taken in conjunction with the accompanying drawings in which:

DESCRIPTION OF THE PREFERRED EMBODIMENTS

Figure 1:
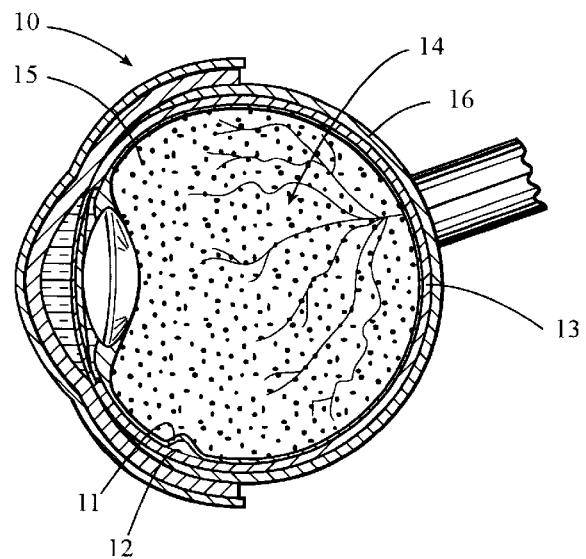
FIG. 1 is a horizontal cross-sectional view of the eye showing a retinal detachment.
Figure 2:
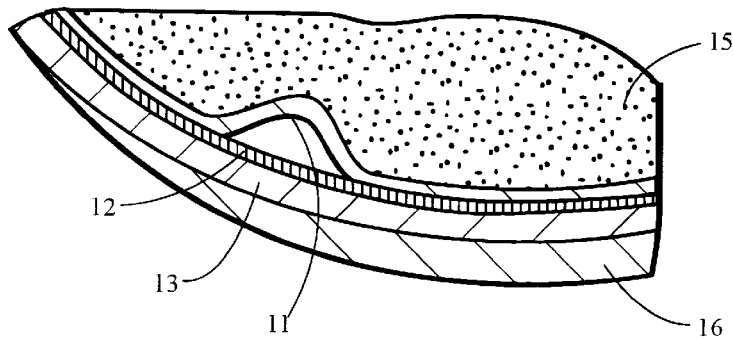
FIG. 2 is a cross-sectional enlarged horizontal view of a portion of the eye illustrating an exemplary presentation of detached retina.

Turning first to FIG. 1, a horizontal cross-sectional view of the eye having a detached retina is shown in pertinent detail. The eye 10 has a retina 11 lining the interior surface thereof Retinal detachment occurs when the retina 11 separates from a very thin subjacent tissue, the retinal pigment epithelium layer 12, adjacent to the outermost side of the retina 11. Beneath of the retinal pigment epithelium is the choroid 13. The interior of the eye comprises the vitreous cavity 14 which is filled with vitreous gel 15. The most common cause of retinal detachment is the liquefaction and shrinkage of the vitreous gel 15 in the vitreous cavity 14. FIG. 2 shows an enlarged portion of the eye 10 of FIG. 1 bearing a detached retina which detached retina is shown in greater detail in relative anatomical relationship with respect to supporting tissues.

Figure 3:
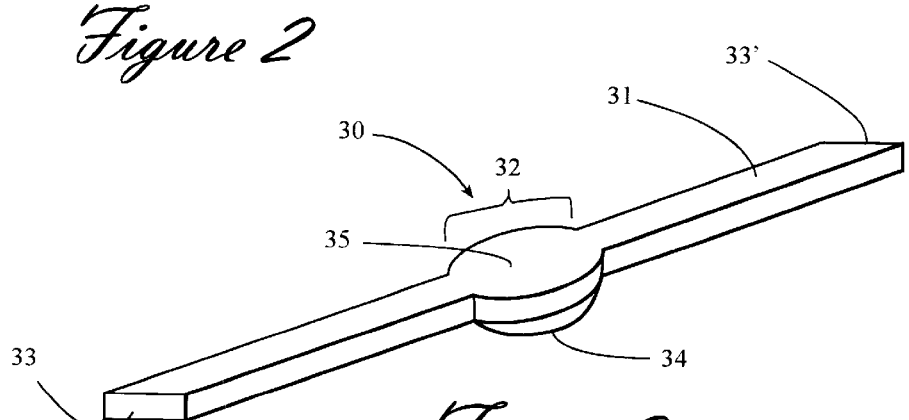
FIG. 3 is a perspective view of a scleral buckling band in accordance with the present invention.

Turning next to FIG. 3, a band in accordance with the resent invention is shown in perspective view. The band 30 comprises an elongate elastomeric strip 31 having a bulbous central portion 32, referred to hereinafter as the differentially compressive portion. The band 30 has two distal ends 33 and 33' projecting laterally from the differentially compressive portion. The differentially compressive portion 32 has a scleral facing apex 34 and a rear surface 35. As used herein, the term "compressive", when used to describe an element or portion of the scleral buckling band, means the change in volume of the element in response to an applied stress. Similarly, the "compressibility" of an element means the ability of an element to be compressed. A "differentially compressive portion" of a band means a segment or portion of a scleral buckling band having a different, usually greater compressibility than other portions of the band.

Figure 4:
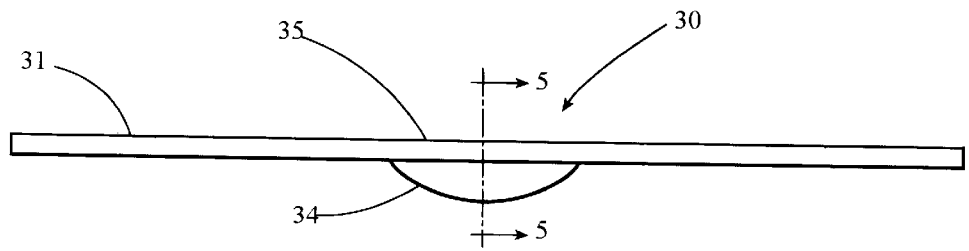
FIG. 4 is a side elevational view of the band of FIG. 3.

The band in accordance with the present invention is shown in horizontal elevational view in FIG. 4. The bulbous nature of the differentially compressive portion 32 (FIG. 3) has an apex 34 representing the portion of the band 30 having the highest circumferential dimension. The band 30 tapers gradually in circumference from the apex 34 diminishing outwardly to the distal ends 33 and 33' of the band 30. This tapering of the band away from the apical portion 34 provides a continuous smooth surface adapted for making smooth, continuous contact with the sclera of the eye.

Figure 5:
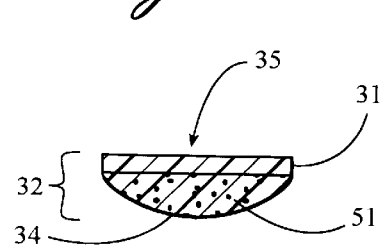
FIG. 5 is a cross-sectional view of the band of FIG. 4 along section line 5—5.

The differentially compressive portion 32 is shown in cross section in FIG. 5. The differentially compressive portion 32 comprises a first compressive material 51 comprising a close-celled foam layer and a second compressive material comprising the less compressive band material 31. The compressibility of the material forming the band portion 31 is different from that of the material 51 forming the differentially compressive foam portion. Thus, the differentially compressive portion 32, when placed against the sclera of the eye, presents a soft, smooth surface to the sclera whereas those portions of the band which contact the sclera distal from the detached retina are smooth, but less compressive.

Figure 6:
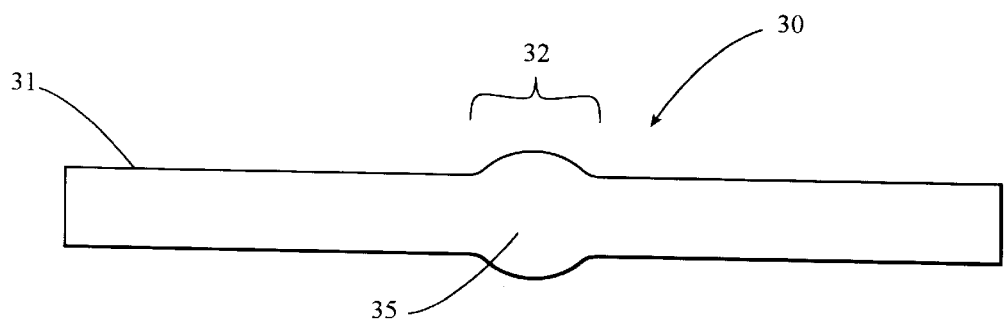
FIG. 6 is a top view of the band of FIG. 3.

FIG. 6 is a top view of the band 30 of FIGS. 3–5. In practice, during retinal reattachment surgery, the band 30 is wrapped circumferentially around the eyeball with the scleral-facing surface 34 of the compressive portion 32 overlying the detached retina 11. The band 30 is distended elastically around the eyeball and the ends 33 and 33' are attached to one another by ligatures or a clasp. The band may then be securely attached to the sclera via strategically placed sutures to prevent post-operative displacement.

Figure 7:
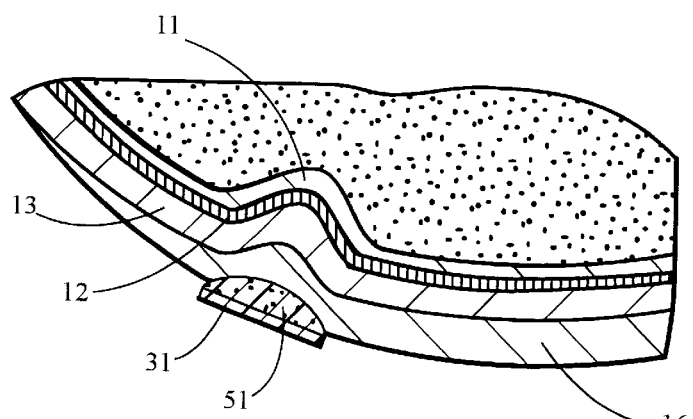
FIG. 7 shows the differentially compressive portion of the band differentially compressing a region of the sclera overlying the retinal detachment.

A close-up, cross-sectional horizontal view of the unitary scleral buckling band 30 in position during repair of a detached retina is shown in FIG. 7. Once the detached retina 11 is juxtaposed with the underlying retinal pigment epithelial layer 12 and choroid 13, a means for welding the retina to the underlying tissue is applied, such as, for example, thermocoagulation or cryotherapy. The scar thus formed firmly adheres the retina to the underlying tissue and prevents the vitreous gel 15 from entering the space between the retina and the underlying tissue.

The device is made by means of extrusion through a two chamber extruder as described, for example in U.S. Pat. No. 5,196,005. A first chamber contains an elastomer which lacks air bubbles. The second chamber contains a silicone foam elastomer. The elastomer compositions contained with the two separate chambers are simultaneously forced through a single die orifice. The extruder includes means for varying the shape and size of the die orifice and thus the extruded article's outer diameter as disclosed, for example, in U.S. Pat. No. 5,511,965. The extruded article is formed as shown in the foregoing embodiments of the invention and cured by vulcanization.

While particular embodiments of the present invention have been illustrated and described, it would be obvious to those skilled in the art that various other changes and modifications can be made without departing from the spirit and scope of the invention. For example, the unitary buckling device may be constructed wherein the differentially compressive portion of the band comprises an elastomer having a different durometer than the remaining portion of the band. Such unitary devices are easily made using the extrusion method discussed above. It is therefore intended to cover in the appended claims all such changes and modifications that are within the scope of this invention.

What I claim is:

1. A scleral buckling band dimensioned to encircle the eye of a person having a detached retina, the scleral buckling band comprising an elastomeric band portion having a length dimensioned to encircle the eye and a differentially compressive portion formed along a portion of said length wherein said band portion and said differentially compressive portion are of unitary construction.

2. The elastomeric band of claim 1 wherein said band portion has a first differentially compressibility and said compressive portion has a second compressibility, and wherein said first compressibility and said second compressibility are different.

3. A scleral buckling band dimensioned to encircle the eye of a person having a detached retina, the scleral buckling band comprising an elongate elastomeric band portion having a length dimensioned to encircle the eye and a differentially compressive portion formed along a portion of said length wherein said elastomeric band portion has a first compressibility and said differentially compressive portion has a second compressibility which is different from said first compressibility, said scleral buckling band having unitary construction.

4. The band of claim 3 wherein said band consists substantially of a non-compressible silicone elastomer and wherein said differentially compressive portion is a closed-cell silicone foam elastomer.

5. The elastomeric band of claim 3 wherein said differentially compressive is portion consists substantially of a close-celled silicone foam elastomer.

* * * * *